(12) United States Patent
Cakmak

(10) Patent No.: US 10,850,100 B2
(45) Date of Patent: Dec. 1, 2020

(54) SYSTEM FOR DECREASING THE BLOOD GLUCOSE LEVEL

(71) Applicant: Yusuf Ozgur Cakmak, Avcilar/Istanbul (TR)

(72) Inventor: Yusuf Ozgur Cakmak, Avcilar/Istanbul (TR)

( * ) Notice: Subject to any disclaimer, the term of this patent is extended or adjusted under 35 U.S.C. 154(b) by 144 days.

(21) Appl. No.: 16/078,287

(22) PCT Filed: Feb. 24, 2016

(86) PCT No.: PCT/TR2016/000016
§ 371 (c)(1),
(2) Date: Aug. 21, 2018

(87) PCT Pub. No.: WO2017/146658
PCT Pub. Date: Aug. 31, 2017

(65) Prior Publication Data
US 2019/0046795 A1    Feb. 14, 2019

(51) Int. Cl.
*A61B 5/145* (2006.01)
*A61N 1/36* (2006.01)
(Continued)

(52) U.S. Cl.
CPC ...... *A61N 1/36031* (2017.08); *A61B 5/14532* (2013.01); *A61B 5/4836* (2013.01);
(Continued)

(58) Field of Classification Search
CPC .. A61B 5/14532; A61B 5/4836; A61N 1/025; A61N 1/0456; A61N 1/36014; A61N 1/36031
See application file for complete search history.

(56) References Cited

U.S. PATENT DOCUMENTS

2006/0190053 A1    8/2006    Dobak, III
2008/0288016 A1    11/2008   Amurthur et al.
(Continued)

FOREIGN PATENT DOCUMENTS

WO    2016/138176 A1    9/2016

OTHER PUBLICATIONS

International Search Report and Written Opinion of corresponding PCT application PCT/TR2016/000016, dated Nov. 22, 2016.
(Continued)

*Primary Examiner* — George Manuel
(74) *Attorney, Agent, or Firm* — Notaro, Michalos & Zaccaria P.C.

(57) ABSTRACT

A blood glucose level decreasing system that decreases blood glucose level of a patient by blocking the sympathetic innervation to liver and pancreas and smooth muscles of the arteries reaching to liver and pancreas with noninvasive electrostimulation of the skin which have the sympathetic nerves originating from the same spinal cord segments. The blood glucose level decreasing system has at least one sensor for measuring the blood glucose level of the patient; at least two electrodes that are placed to skin dermatomal of the patient; at least one stimulator that sends electrical signals to the electrodes to block the sympathetic nerve innervation to smooth muscles of hepatic artery proper and liver, and expand liver artery of the patient; and at least one control unit, which receives the blood glucose level from the sensor, compares received level with a predetermined threshold value and controls the stimulator according to the result.

24 Claims, 2 Drawing Sheets

(51) Int. Cl.
    *A61N 1/04*    (2006.01)
    *A61N 1/02*    (2006.01)
    *A61B 5/00*    (2006.01)

(52) U.S. Cl.
    CPC ............ *A61N 1/025* (2013.01); *A61N 1/0456* (2013.01); *A61N 1/36014* (2013.01)

(56) References Cited

U.S. PATENT DOCUMENTS

| | | |
|---|---|---|
| 2009/0088816 A1 | 4/2009 | Harel et al. |
| 2012/0303098 A1* | 11/2012 | Perryman .......... A61N 1/36057 607/62 |
| 2015/0073510 A1 | 3/2015 | Perryman |

OTHER PUBLICATIONS

International Preliminary Report on Patentability and response to Written Opinion, dated May 17, 2018.

\* cited by examiner

SYSTEM FOR DECREASING THE BLOOD GLUCOSE LEVEL

FIELD OF INVENTION

The present invention relates to a system for decreasing blood glucose level in order to treat hyperglycemia.

PRIOR ART

Hyperglycemia is a medical condition, in which glucose level of the blood plasma is relatively high (for example higher than 11.1 mmol/l or 200 mg/dl). Hyperglycemia may cause ketoacidosis (contrast ketosis) disease or heart diseases if it is not treated. In other words, if hyperglycemia is not treated properly, patient would be harmed severely.

There are several reasons of hyperglycemia. Some of them are diabetes mellitus, diet of the patient, using some drugs and stress.

Researches show that in most of the cases, operation efficiency of the liver and pancreas are directly and kidney is indirectly related with the glucose level of the blood. Liver can store and release glucose, and this stored form of glucose called glycogen.

Although medications reduce glucose level of the blood in some cases, because of the side effects of the medications, this treatment method is not preferred by some patients.

Moreover, in some cases, medications are unable to treat hyperglycemia.

Another solution for improving operation efficiency of the liver is to block sympathetic nerve stimulation to liver by invasive radiological techniques like intraarterial radioablation or direct electrostimulation of liver arteries. Patent document US2006190053A1 discloses neural blockage for treatment of metabolic syndrome and type 2 diabetes. According to this document, sympathetic nervous system of a patient is blocked in order to alleviate hyperglycemia states. In order to block sympathetic nervous system, implanted electrodes are used. However, according to this document, a medical surgery is required in order to implant said electrodes.

Brief Description of Invention

Present application discloses a blood glucose level decreasing system that decreases blood glucose level of a patient by sympathetic nerve blockade to liver and pancreas with stimulation of the skin segment (dermatome) that have the sympathetic nerves originating in the same segments related to liver and pancreas with a specific range of frequency that can block the sympathetic innervation to the liver and pancreas in addition to smooth muscles of the pancreas and liver arteries like common hepatic artery and hepatic artery proper.

Said blood glucose level decreasing system comprises at least one sensor for measuring the blood glucose level of said patient; at least two electrodes that are placed to skin dermatomal of said patient; at least one stimulator that sends electrical signals to said electrodes in order to block the sympathetic nerve innervation to smooth muscles of hepatic artery proper and liver, and expand the common hepatic artery and hepatic artery proper of the patient; and at least one control unit, which receives the blood glucose level from said sensor, compares received level with a predetermined threshold value and control said stimulator according to the result of said comparison.

According to the present application, since electrodes are placed above the dermatomes (in other words since electrodes are placed to the skin), blood glucose level decreasing system is used by the patients easily. Moreover, according to the present application, nerves or arteries of the patient are not damaged and the system blocks the sympathetic innervation to liver and pancreas non-invasively and in a reversible manner. Therefore, blood glucose level of the patient is reduced easily and without causing any damage to the nerve so that the human body and sympathetic nerve system can still react to hypoglisemic states.

OBJECT OF INVENTION

Object of the present application is to provide a non-invasive system for decreasing the blood glucose level of a patient.

Another object of the present application is to provide a wearable system.

Another object of the present application is to provide a system that measures blood glucose level of a patient and reduce blood glucose level of the patient if measured value is above a predetermined threshold value.

DETAILED DESCRIPTION OF INVENTION

Figure 1:
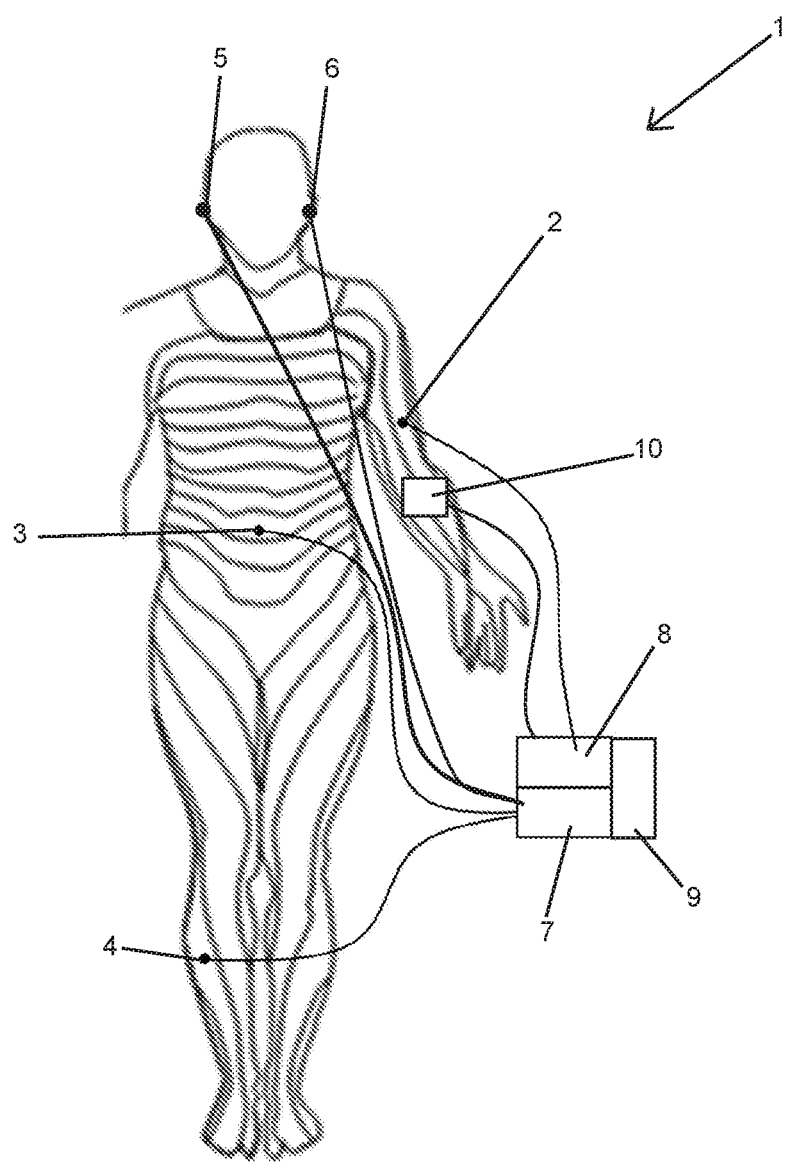
FIG. 1 is an overview representation of various components of the system and their arrangement when implemented on the body of a user.
Figure 2:
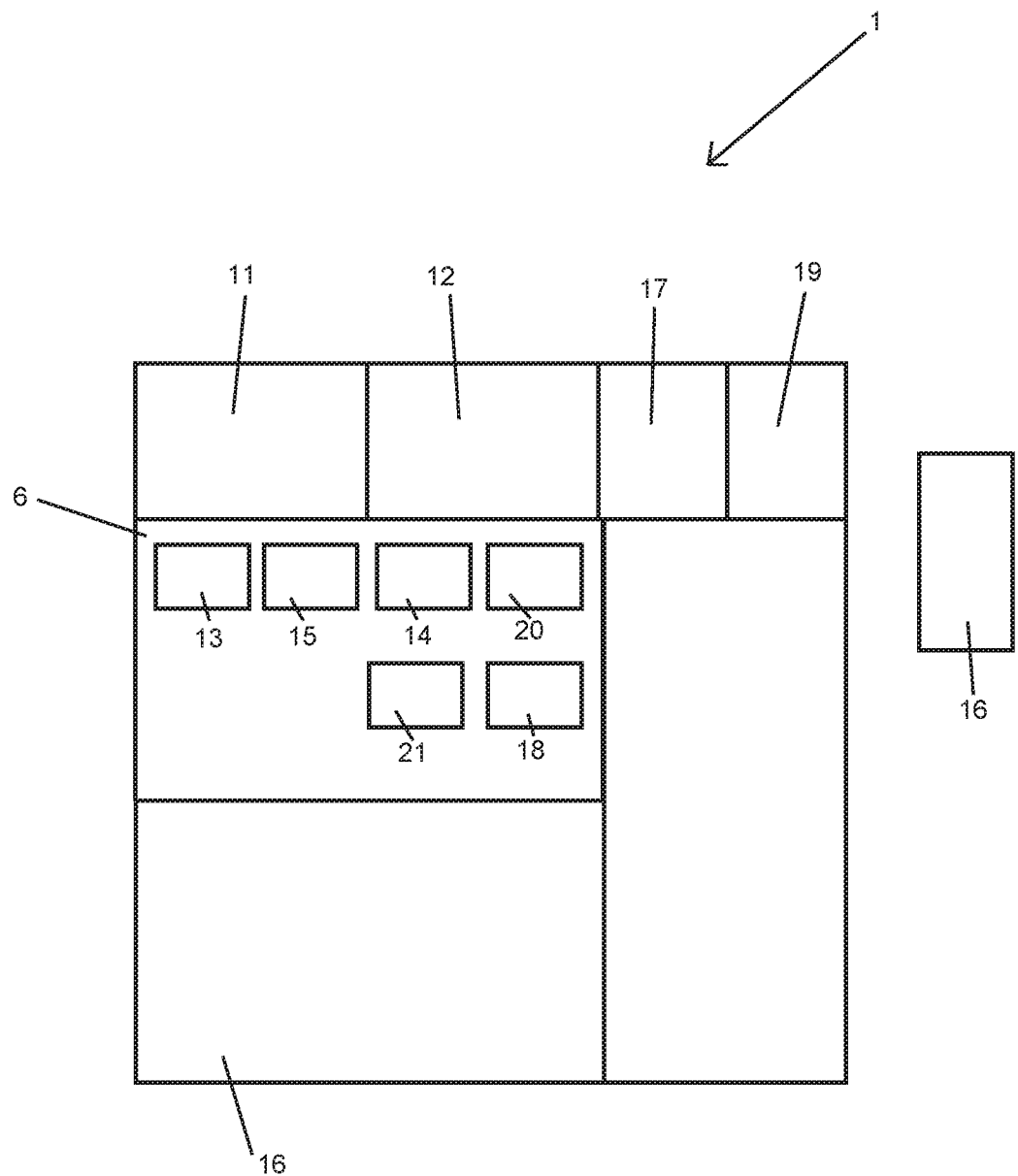
FIG. 2 is schematic representation of the various components of the system

Hyperglycemia is a dangerous medical condition, which may cause ketoacidosis or heart diseases if it is not treated. One of the reasons of the hyperglycemia is increased sympathetic stimulation to liver and pancreas accompanied by constriction of those organ's arteries. Therefore, in the present application, a system for noninvasively blocking the sympathetic innervation to liver and pancreas that results with the increased blood flow to liver and pancreas and decreasing of the blood glucose level in order to treat hyperglycemia.

Blood glucose level decreasing system 1 of the present application decreases blood glucose level of a patient by blocking the sympathetic innervation to liver and pancreas temporarily and in the long term it can induce neuronal plasticity so that the sympathetic system based blood glucose increases can be modified. Said system comprises, at least one sensor 2 for measuring the blood glucose level of said patient; at least two electrodes 3, 4 that are placed to skin dermatomal (a skin area that is supplied by a nerve) of said patient; at least one stimulator 7 that sends electrical signals to said electrodes 3, 4 in order to block the autonomic nerve innervation but especially the sympathetic nerve innervation to smooth muscles of hepatic artery proper, liver and pancreas, and expand common hepatic artery, hepatic artery proper, superior mesenteric artery of the patient; and at least one control unit 8, which receives the blood glucose level from said sensor 2, compares received level with a predetermined threshold value and control said stimulator 7 according to the result of said comparison. Said system may further comprise at least one power source 9 (for example a rechargeable battery) for energizing the control unit 8 and/or electrodes 3, 4. In an alternative embodiment, blood glucose level decreasing system comprises a power generator 10 that generated electrical power from the body (skin) of the user for energizing the control unit 8 and/or electrodes.

In a preferred embodiment of the present application, said signal has frequency 1-60 Hz (more preferably 10 Hz) a burst frequency of 50-120 Hz with 1-10 Hz frequency. Current of the signal is preferably between 10-20 mA (more preferably 15 mA). Voltage of the signal is preferably between 1-15 V (more preferably 5 V). Duration of the signal is preferably between 0.1-300 μs (more preferably 100 μs).

In an exemplary embodiment of the present application, said electrodes 3, 4 are placed over the T7-S2 dermatomes (preferably T10 and/or L5) to stimulate related nerves. One of said electrodes 3, 4 are used as anode and other one is used as cathode. Then, blood glucose level measured by said sensor 2 is sent to said control unit 8. In the control unit, blood glucose level is compared with a predetermined threshold value (for example 11.1 mmol/l or 200 mg/dl). If measured level is higher than said threshold value, control unit 8 enables said stimulator 7 to send electrical signals to the electrodes 3, 4. When the nerves on said dermatome are excited with the signal, sympathetic innervation to smooth muscles of hepatic artery proper and liver itself is blocked (so that the neuronal communication of the liver and central autonomic nerve system will be blocked and as a consequence there will not be influences of the central sympathetic outflow to liver or liver's feedback to central autonomic nerve system to increase blood glucose level with neuroendocrine response like glycogenolysis). In other words, said signal with specific frequency blocks the neural connection between the autonomic nerve system and liver, and overcomes extreme stimulations to liver that may drive liver to secrete more glucose to the blood which is a common phenomenon in the case of a fight or flight response.

It has been shown that direct electrical stimulation of the sympathetic nerves (splanchnic nerves) that reaches to liver over the liver arteries (first over the common hepatic artery and then through the hepatic artery proper) and also stimulating their wall of smooth muscles decreases liver glycogen content and causes an increased release of glucose (glycogenolysis) by increasing the activity of the liver glycogen phosphorylase and glucose-6-phosphatase enzymes and as well as a partial inactivation of phosphorylase phosphatase activity. The sympathetic splanchnic nerves innervating the liver originate from neurons in the celiac and superior mesenteric ganglia, which are innervated by pre-ganglionic neurons located in the intermediolateral column of the spinal cord (T7-T12) and the same spinal segments of sympathetic nerve system also gives collateral branches to related skin segments, dermatomes. In addition to sympathetic innervation of liver, the sympathetic nerves on the coeliac trunk pass to the common hepatic artery and then they elongates into the pancreas after giving branches to liver with the aid hepatic artery proper. Sympathetic innervation to pancreas inhibits pancreatic beta cells to secrete insulin and aid to keep the state of hyperglycemia. Overall, the blockage of the sympathetics over the common hepatic artery do not only act over the liver by blocking glucogenolysis (glucose production and secretion to blood) but also act through the pancreas by blocking the inhibitory action of sympathetic nerve system over insulin secretion, so that insulin can be secreted to the blood to take the glucose to tissues. Moreover, sympathetic stimulation to pancreas also increases glucagon secretion from pancreas, and the glucagon hormone which acts on liver cells that have its receptors and stimulates gluconeogenesis (new glucose synthesis) and glycogenolysis (production of glucose from glucogen storages) so that blood glucose elevates. In the case of a sympathetic blockade over the common hepatic artery, not only the sympathetic blockade to liver but to the pancreas obtained, so that in addition to overcome insulin secretion blockade and improvement of the insulin secretion obtained. Moreover glucagon secretion is also blocked and as a consequence dual action to decrease blood glucose obtained through pancreas in addition to liver. Glucagon is also act on kidney to produce glucose via gluconeogenesis (new glucose production) so that blockade of sympathetic nerves over the common hepatic artery with corresponding skin stimulation is also blocks the glucose production of kidney with aid of glucagon blockade in the pancreas.

Moreover, the sympathetic nerve system also reaches to pancreas with the aid of superior mesenteric artery, a branch of abdominal aorta. 0.5 cm below the coeliac trunk of which the common hepatic artery originates. The segmental skin stimulation also blocks the sympathetics on the superior mesenteric artery so that it effects the dual sympathetic innervation to pancreas: through common hepatic artery and through superior mesenteric artery.

Since the sympathetic nerves to liver and pancreas pass through the arteries, common hepatic artery and hepatic artery proper, they also stimulate the smooth muscles of those arteries. So in the case of a sympathetic nerve blockade, the smooth muscles of the arterial walls cannot be stimulated and as a consequence the dilatation of the arteries is observed. Our researches revealed the dilatation of those arteries with the segmental skin stimulation. The diameter, volume flow and pulsatility index of the arterial responses were detected by Doppler ultrasound technique during skin stimulation (table1).

In addition to blockade of related sympathetic to liver and pancreas with corresponding skin stimulation, the stimulation of the parasympathetic nerve system (vagus) to pancreas can stimulate beta cells and secretion of insulin to blood. In the case of a sole sympathetic blockade to liver and pancreas, the glucose levels in the blood can be decreased but the effect can be boosted with the aid of vagal stimulation.

Parasympathetic nerve system (vagus nerve) to liver also accelerates the glycogen synthesis (glyconeogenesis) in liver, so that it works for storage instead of secreting the glucose to blood. The vagus nerve has its cutaneous branches only in the ear skin, specifically concha area and external auditory canal. The vagus nerve can directly stimulated from the ear skin area as well as with indirect way of stimulations like: median and common peroneal nerve stimulation, decreasing breath rate and ocular compression.

Therefore, in another preferred embodiment of the present application, blood glucose level decreasing system comprises at least two additional electrodes 5, 6 that are placed the ear skin, median nerve and peroneal nerves' territories in order to stimulate the parasympathetic nerve system (vagus nerve) to liver in addition to guided systems for decreasing the breathing rate or ocular compression. Frequency of the signal sent to said additional electrodes is 1-100 Hz (more preferably 2-10 Hz) or a burst frequency of 50-120 Hz with 1-10 Hz frequency.

The fight or flight response can be triggered easily in some cases who have lower thresholds and it can result with the unnecessary increased blood glucose. Moreover, thanks to said signal, hepatic artery proper of the patient is expanded which is a proof of functional denervation of the hepatic artery (hepatic artery proper) and liver, so that liver became numb to autonomic stimulation.

In another preferred embodiment of the present application, blood glucose level decreasing system comprises one set of electrodes 3, 4 (for example an electrode pair) that are placed over the L5 dermatomes and another set of electrodes (for example an electrode pair) that are placed over the T10 dermatomes. In this embodiment, signals sent to different set of electrodes are able to be controlled separately (for example frequency and or voltage level of the electrodes placed over the L5 dermatomes can be different from the frequency and or voltage level of the electrodes placed over the T10 dermatomes). By controlling said set of electrodes separately, blood glucose level reduction effect of the system is boosted.

In another preferred embodiment of the present application, blood glucose level decreasing system comprises at least one screen 11. Said screen informs user about blood glucose level that measured by said sensor and/or operation status of the stimulator (for example signal parameters).

Optimum signal parameters for reducing the blood glucose level may vary for different individuals. Said parameters may depend on age, weight, height and gender of the patient. Therefore, in another preferred embodiment of the present application, blood glucose level decreasing system comprises at least one input means 12 (for example a keyboard or a touchscreen) to control signal parameters. In an exemplary embodiment, users are able to enter their age, weight, height, and gender information through said input means. In another exemplary embodiment, users directly changes optimum signal parameters manually. In order to change said parameters manually, optimum parameters for one individual may be found by a physician prior to use of the blood glucose level decreasing system.

In another preferred embodiment of the present application, said control unit comprises means for monitoring the current level of the signal 13 that are sent to said electrodes. In this embodiment, if the current level drops below a predetermined level, control unit 8 increases the voltage of the signal in order to increase the current level above said predetermined level. Therefore, it is ensured that current level of the signal is high enough to block the autonomic innervation. In alternative embodiments, said control unit 8 may comprise means for monitoring the frequency and/or wavelength (duration) of the signal 14. Therefore, it is ensured that signal parameters are correct.

In another embodiment, control unit comprises at least one short circuit control element 15. In this embodiment, if a short circuit situation occurs (for example because of misplacing the electrodes); signal sent to the electrodes is cut. Therefore, damaging the electrodes or control unit 8 is prevented.

In another embodiment of the present application, blood glucose level decreasing system 1 of the present application comprises at least one remote control unit 16 and at least one transmitter 17, which receives commands from said remote control unit 16 and control the control unit 8 according to the received commands. In this embodiment, by using remote control unit 16, said signal could be sent to the electrodes manually even if blood glucose level of a patient is not higher than said predetermined threshold value. Therefore, it is prevented that blood glucose level of a patient increases above a dangerous level during a critical operation (for example during a surgery). In another preferred embodiment of the present application, control unit 8 comprises at least one open circuit control element 18. In this embodiment, if electrical connection between electrodes is cut (for example because of damaging at least one electrode) users are able to be notified. In order to notify the user, blood glucose level decreasing system comprises at least one alarming unit 19 (for example a buzzer or a warning light).

In another preferred embodiment of the present application, each of said electrodes comprises an anode or a cathode connection and a pair of anode and cathode connection. In this embodiment, said electrodes are called intelligent electrodes. During the normal use of the blood glucose level decreasing system, anode connection of one electrode and cathode connection of other electrode is used for transmitting signals to the dermatomes. If any open circuit situation occurs, for example if one of the electrodes is damaged, signal is transmitted to the dermatomes through pair of anode and cathode connection of other electrode.

In another preferred embodiment of the present application, blood glucose level decreasing system 1 comprises at least one temperature sensor 20, which measures the temperature of the electrodes and skin of the user, and at least one temperature adjusting unit 21, which adjusts the temperature of the electrode according to the temperature values measured by said temperature sensor. In this embodiment, if temperature of the electrode is higher than the temperature of the skin of the user, said temperature adjusting unit 21 decreases the temperature of the electrode. Similarly, if temperature of the electrode is lower than the temperature of the skin of the user, said temperature adjusting unit 21 increases the temperature of the electrodes. Therefore, it is ensured that said electrodes do not damage the skin of the user because of a high or low temperature.

Results of an experiment of the present application are shown in table 1. In this experiment, blood glucose level decreasing system of the present application is used on 5 different patients. According to this experiment, it is shown that when a 10 Hz signal is sent to the electrodes, diameters of the hepatic artery proper and common hepatic artery of the patient and blood flow speed are increased.

TABLE 1

| | | 1 | | 2 | | 3 | | 4 | | 5 | |
|---|---|---|---|---|---|---|---|---|---|---|---|
| | | Pre | Post | Pre | Post | Pre | Post | Pre | Post | Pre | Post |
| Hepatic Artery Proper | Vol. Flow (ml/min) | 111.4 | 133.2 | 130.8 | 176.7 | 96.6 | 135.7 | 149 | 175 | 122.5 | 165.7 |
| | Diameter (cm) | 0.31 | 0.33 | 0.3 | 0.31 | 0.3 | 0.33 | 0.3 | 0.3 | 0.3 | 0.31 |
| | Pulsatility Index (PI) | 2.89 | 2.66 | 3.04 | 2.68 | 2.24 | 2.04 | 1.71 | 1.33 | 1.65 | 1.21 |
| Common Hepatic Artery | Vol. Flow (ml/min) | 937 | 1291 | 1120 | 1601 | 644 | 935.6 | 863.8 | 1441 | 1180 | 1256 |
| | Diameter (cm) | 0.51 | 0.63 | 0.61 | 0.74 | 0.43 | 0.63 | 0.55 | 0.61 | 0.64 | 0.7 |
| | Pulsatility Index (PI) | 2.01 | 1.67 | 1.49 | 1.45 | 1.49 | 1.19 | 2.71 | 1.65 | 1.21 | 1.2 |

According to the present application, since electrodes are placed above the dermatomes (in other words since electrodes are placed to the skin), blood glucose level decreasing system is used by the patients easily. Moreover, according to the present application, nerves or arteries of the patient are not damaged. Therefore, blood glucose level of the patient is reduced easily and without causing any damage.

The invention claimed is:

1. A blood glucose level decreasing system for decreasing blood glucose level of a patient by blocking the sympathetic innervation to liver and pancreas temporarily and expanding the arteries of the patient, characterized by comprising;
    at least one sensor for measuring the blood glucose level of said patient;
    at least two electrodes that are suitable to be placed over T10 and/or L5 dermatomes of said patient;
    at least one stimulator for sending electrical signals to said electrodes in order to block the sympathetic nerve innervation to smooth muscles of hepatic artery proper, liver and pancreas, and for expanding common hepatic artery, hepatic artery proper and superior mesenteric artery of the patient and
    at least one control unit, for receiving the blood glucose level from said sensor, comparing received level with a predetermined threshold value and controlling said stimulator according to the result of said comparison,
    characterized in that the blood glucose level decreasing system comprises one set of electrodes that are placed over the L5 dermatomes and another set of electrodes that are placed over the T10 dermatomes.

2. A blood glucose level decreasing system according to claim 1, characterized in that; said signal has frequency 1-60 Hz.

3. A blood glucose level decreasing system according to claim 2, characterized in that; said signal has frequency 10 Hz.

4. A blood glucose level decreasing system according to claim 1, characterized in that; said signal has frequency has a burst frequency of 50-120 Hz with 1-10 Hz frequency.

5. A blood glucose level decreasing system according to claim 1, characterized in that; current of the said signal is between 10-20 mA.

6. A blood glucose level decreasing system according to claim 1, characterized in that; current of the said signal is 15 mA.

7. A blood glucose level decreasing system according to claim 1, characterized in that; voltage of said signal is between 1-15 V.

8. A blood glucose level decreasing system according to claim 1, characterized in that; voltage of said signal is 5 V.

9. A blood glucose level decreasing system according to claim 1, characterized in that; duration of said signal is between 0.1-300 µs.

10. A blood glucose level decreasing system according to claim 1, characterized in that; duration of said signal is 100 µs.

11. A blood glucose level decreasing system according to claim 1, characterized by further comprising; at least one power source for energizing the control unit and/or electrodes.

12. A blood glucose level decreasing system according to claim 1, characterized by further comprising; at least one power generator that generated electrical power from the body of the user for energizing the control unit and/or electrodes.

13. A blood glucose level decreasing system according to claim 1, characterized by further comprising; at least one screen.

14. A blood glucose level decreasing system according to claim 1, characterized by further comprising; at least one input means.

15. A blood glucose level decreasing system according to claim 1, characterized in that; said control unit comprises means for monitoring the current level of the signal that are sent to said electrodes.

16. A blood glucose level decreasing system according to claim 1, characterized in that; control unit comprises at least one short circuit control element.

17. A blood glucose level decreasing system according to claim 1, characterized by further comprising; at least one remote control unit and at least one transmitter, which receives commands from said remote control and control the control unit according to the received commands.

18. A blood glucose level decreasing system according to claim 1, characterized in that; control unit comprises means for monitoring the frequency of the signal.

19. A blood glucose level decreasing system according to claim 1, characterized in that; control unit comprises means for monitoring the wavelength of the signal.

20. A blood glucose level decreasing system according to claim 1, characterized in that; control unit comprises at least one open circuit control element.

21. A blood glucose level decreasing system according to claim 20, characterized by further comprising; at least one alarming unit.

22. A blood glucose level decreasing system according to claim 1, characterized in that; each of said electrodes comprises an anode or a cathode connection and a pair of anode and cathode connection.

23. A blood glucose level decreasing system according to claim 1, characterized by further comprising; at least one temperature sensor, which measures the temperature of the electrodes and skin of the user, and at least one temperature adjusting unit, which adjusts the temperature of the electrode according to the temperature values measured by said temperature sensor.

24. A blood glucose level decreasing system according to claim 1, characterized by further comprising; at least two additional electrodes that are placed the ear skin.

* * * * *